United States Patent [19]

Biedermann et al.

[11] 4,443,464

[45] Apr. 17, 1984

[54] (+)-2-[1-(2,6-DICHLOROPHENOXY)-ETHYL]-1,3-DIAZACYCLOPENT-2-ENE AND THE METHOD FOR THE TREATMENT OF HUMAN BEINGS SUFFERING FROM NERVOUS DISARRANGEMENTS, IN PARTICULAR MIGRAINE

[75] Inventors: Jürgen Biedermann, Pulheim-Stommeln; Gerrit Prop, Pulheim; Ille-Stephanie Doppelfeld, Bergheim-Giessen, all of Fed. Rep. of Germany

[73] Assignee: A. Nattermann & Cie GmbH, Cologne, Fed. Rep. of Germany

[21] Appl. No.: 367,944

[22] Filed: Apr. 13, 1982

[30] Foreign Application Priority Data

Dec. 10, 1981 [DE] Fed. Rep. of Germany ....... 3149010

[51] Int. Cl.$^3$ ............................................ A61K 31/415

[52] U.S. Cl. .................................................. 424/273
[58] Field of Search ..................... 424/273 R; 548/359

[56] References Cited

U.S. PATENT DOCUMENTS 3,966,757  6/1976  Baganz et al. .................. 260/309.6
4,025,539  5/1977  Baganz et al. ..................... 424/273

Primary Examiner—Stanley J. Friedman
Attorney, Agent, or Firm—Pearne, Gordon, Sessions, McCoy, Granger & Tilberry

[57] ABSTRACT

This invention relates to (+)-2-[1-(2,6-dichlorophenoxy)-ethyl]-1,3-diazacyclopent-2-ene and to pharmaceutically acceptable acid addition salts thereof and the method for the treatment of human beings suffering from nervous disarrangements, in particular migraine, using these compounds.

4 Claims, No Drawings

(+)-2-[1-(2,6-DICHLOROPHENOXY)-ETHYL]-1,3-DIAZACYCLOPENT-2-ENE AND THE METHOD FOR THE TREATMENT OF HUMAN BEINGS SUFFERING FROM NERVOUS DISARRANGEMENTS, IN PARTICULAR MIGRAINE

This invention relates to (+)-2-[1-(2,6-dichlorophenoxy)-ethyl]-1,3-diazacyclopent-2-ene corresponding to formula I:

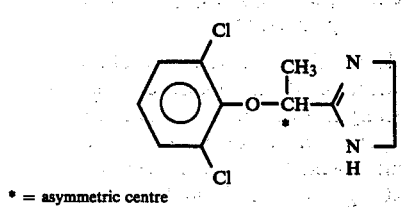

* = asymmetric centre and to the pharmaceutically acceptable acid addition salts thereof, to processes for the production of this compound and to the use thereof as active substance in pharmaceutical compositions having valuable pharmacological properties, that is, primarily having therapeutic effects on the central nervous system.

Processes for the production of the racemic compound (+)-2-[1-(2,6-dichlorophenoxy)-ethyl]-1,3-diazacyclopent-2-ene which is known as an anti-hypertonic, are described in U.S. Pat. Nos. 3,966,759 and 4,025,539.

Although it was known that 2-[1-(2,6-dichlorophenoxy)-ethyl]-1,3-diazacyclopenten-2-ene can exist in two optically active enantiomeric forms by virtue of the asymmetrically substituted carbon atom, the optically active levorotatory or dextrorotatory enantiomers have hitherto not been separated or produced.

Separation of the dextrorotatory enantiomers to elucidate the relation between optical activity and biological activity has been achieved by a known resolution method using dextrorotatory dibenzoyl tartaric acid.

Surprisingly, pharmacological tests on the dextrorotatory enantiomer have shown a CNS-depressant effect, with the blood pressure-reducing effect no longer present.

The synthesis of the optically active compound according to the present invention is characterised in that it is based on optically active starting materials. Thus, for example, a (+)-2-hydroxypropionic acid-$C_{1-4}$ alkyl ester is reacted with excess thionylchloride in the presence of catalytic quantities of dimethylformamide with configuration reversal to produce a (−)-2-chloropropionic acid-$C_{1-4}$ alkyl ester. The subsequent etherification with 2,6-dichlorophenol takes place with another configuration reversal in suitable organic solvents, for example acetonitrile, butanone, or dimethylformamide, in the presence of a base, for example sodium hydride, alkalimethylate, alkaliethylate or 1,4-diazabicyclo-(2,2,2)-octane at a temperature in the range of from 60° to 150° C., preferably at 80° C., to produce a $C_{1-4}$ alkylester of (+)-2-(2,6-dichlorophenoxy)-propionic acid which, as well as the functional acid derivatives thereof, is used as starting material for the synthesis of 1,3-diazacyclopentene derivatives. The reaction may be carried out with ethylene diamine itself or with a reactive N-derivative of ethylene diamine, or with ammonia or an ammonia-releasing agent together with a compound which may be converted into ethylene diamine by treating with ammonia. The following, for example, may be used as functional acid derivatives: $C_{1-4}$ alkylesters, acid halides, amides, thiamides, amidines, imido acid esters or the nitrile of 2-(2,6-dichlorophenoxy)-propionic acid.

In the present process, (+)-2-(2,6-dichlorophenoxy)-propionic acid ethylester is reacted with a considerable excess of 1,2-diaminoethane at room temperature and is converted into (+)-2-(2,6-dichlorophenoxy)-propionic acid-N-(2-aminoethyl)-amide which, for its part is dehydrated or cyclised with a titanium tetrachloride/tetrahydrofuran complex in chloroform in the presence of 4-dimethylaminopyridine at from 0° to 30° C. into (+)-2-[1-(2,6-dichlorophenoxy)-ethyl]-1,3-diazacyclopent-2-ene.

The dextrorotatory base is then converted into a physiologically acceptable acid addition salt using a suitable organic or inorganic acid in a lower alcohol. Thus, (+)-2-[1-(2,6-dichlorophenoxy)-ethyl]-1,3-diazacyclopent-2-ene hydrochloride is obtained from the (+) base, for example using propan-2-ol/hydrogen chloride.

Another process is also based on (+)-2-(2,6-dichlorophenoxy)-propionic acid ethylester which is reacted with an ethanolic solution of ammonia at room temperature and is converted in to (−)-2-(2,6dichlorophenoxy)-propionic acid amide which is difficultly soluble in ethanol. This amide is dehydrated at from 0° to 30° C. with a titanium tetrachloride/tetrahydrofuran complex and 4-methyl-morpholine in chloroform into (+)-2-(2,6-dichlorophenoxy)-propionic acid nitrile. By introducing hydrogen chloride at 0° C., the nitrile is then converted with ethanol in chloroform into (+)-2-(2,6-dichlorophenoxy)-propionimido acid ethylester hydrochloride, this compound is dissolved in ethanol and is cyclised by adding 1,2-diaminoethane to produce (+)-2-[1-(2,6-dichlorophenoxy)-ethyl]-1,3-diazacyclopent-2-ene. Analogously to the previous process, (+)-2-[1-(2,6-dichlorophenoxy)-ethyl]-1,3-diazacyclopent-2-ene hydrochloride is produced from the (+) base thus obtained.

The resolution of the (+)-2-[1-(2,6-dichlorophenoxy)-ethyl]-1,3-diazacyclopent-2-ene takes place in a known manner according to processes which are conventional in organic chemistry (resolution: see survey in Houben-Weyl, Methoden der organischen Chemie, Vol. 4/2, 505 (1955); Georg Thieme Verlag, Stuttgart). The racemic base is converted in a suitable solvent, for example acetone, using optically active (+)-dibenzoyl tartaric acid, into two diastereomeric salt pairs which differ from each other in their solubility. The salt which is crystallised in acetone due to the low solubility thereof, and in which the (+) base (+)-2-[1-(2,6-dichlorophenoxy)-ethyl]-1,3-diazacyclopent-2-ene is present in a greatly concentrated form as the (+)-dibenzoyltartrate is filtered with suction, the (+) base is released using saturated sodium carbonate solution and is again mixed with (+)-dibenzoyl tartaric acid in acetone. The second crystallisate which is obtained in this manner is present as the (+)-dibenzoyl tartrate of the (+) base which, in the meantime, is greatly concentrated and is further purified by being crystallised twice from ethanol. The (+) base is released using sodium carbonate solution and is converted into the optically pure (+)-2-[1-(2,6-dichlorophenoxy)-ethyl]-1,3-diazacyclopent-2-ene hydrochloride using propan-2-ol hydrogen chloride.

Many varied pharmaceutically acceptable acid addition salts may be obtained from the compound according to the invention in the form of the free base, by treating with suitable acids according to conventional methods. The following, for example, are suitable for the production of such salts: inorganic acids, for example hydrobromic acid, sulphuric acid or phosphoric acid, or organic acids, for example acetic acid, glycolic acid, succinic acid, fumaric acid, malic acid, tartaric acid, citric acid, benzoic acid or cinnamic acid.

The compounds according to the present invention have valuable pharmacological properties, that is, primarily therapeutic effects on the central nervous system, and they must be used as active substances in drugs which have a spasmolytic or sedative effect. Thus, the preparations according to the present invention may be used for the treatment of human beings suffering from nervous disarrangements, in particular migraine.

The present invention also relates to preparations which contain the compound corresponding to formula I or contain pharmaceutically applicable acid addition salts of this compound. The pharmaceutical preparations according to the present invention are preparations for enteral, such as oral or rectal, and for parenteral administration, and contain the pharmacological active substance on its own or together with a conventional, pharmaceutically acceptable carrier. The pharmaceutical preparations containing the active substance are advantageously in the form of individual doses which correspond to the required method of administration, for example tablets, coated tablets, capsules, suppositories, granules, solutions, emulsions or suspensions. The dosage of the compound usually ranges from 0.05 to 50 mg per dose, preferably from 0.075 to 0.1 mg per dose and may be administered once or several times.

The production of the compounds according to the present invention is explained in more detail by the following Examples. The melting points which are specified in the Examples were measured using a Büchi 510 melting point apparatus and are specified in °C. and are uncorrected.

EXAMPLE 1

Synthesis of
(+)-2-[1-(2,6-dichlorophenoxy)-ethyl]-1,3-diazacyclopent-2-ene hydrochloride (−)-2-chloropropionic acid ethylester 260 g ($\triangleq$2.202 mols) of (+)-2-hydroxypropionic acid ethylester $[\alpha]_D^{20} = +11.3°$ (undiluted are chlorinated with 274.0 g (=2.303 mols) of thionylchloride in the presence of 1.5 ml of dimethylformamide at boiling temeprature. 90.0 g of (−)-2-chloropropionic acid ethylester $C_5H_9ClO_2$ [136.6] are obtained. Bp: 142°–143° C. $[\alpha]_D^{20} = -19.4°$ (undiluted).

(+)-2-(2,6-dichlorophenoxy)-propionic acid ethylester 70.0 g ($\triangleq$0.429 mols) of 2,6-dichlorophenol are heated to boiling point in 300 ml of butanone with 40.6 g ($\triangleq$0.579 mols) of potassium ethylate and 81.0 g ($\triangleq$0.593 mols) of (−)-2-chloropropionic acid ethylester for 48 hours, with stirring and under reflux. After working up, 64.0 g of (+)-2-(2,6-dichlorophenoxy)-propionic acid ethylester $C_{11}H_{12}Cl_2O_3$ [263.1] are obtained, $Bp_{0.1}$: 111°–112° C. $[\alpha]_D^{20} = +36.8°$ (undiluted)

(+)-2-(2,6-dichlorophenoxy)-propionic acid-N-(2-aminoethyl)-amide 42.0 g ($\triangleq$0.160 mols) of (+)-2-(2,6-dichlorophenoxy)-propionic acid ethylester are stirred for 6 hours at room temperature with 194.0 g ($\triangleq$3.228 mols) of 1,2-diaminoethane and, after working up, produce 34.0 g of (+)-2-(2,6-dichlorophenoxy)-propionic acid-N-(2-aminoethyl)amide, $C_{11}H_{14}Cl_2N_2O_2$ [277.2] as a high viscosity oil, $[\alpha]_D^{20} = +5.6°$ (c=1/ethanol).

(+)-2-[1-(2,6-dichlorophenoxy)-ethyl]-1,3-diazacyclopent-2-ene 50.2 g ($\triangleq$0.2646 mols) of titanium tetrachloride are dissolved in a mixture of 700 ml of absolute chloroform and 25 ml of tetrahydrofuran at 0° C. and are mixed with 30.0 g ($\triangleq$0.108 mols) of (+)-2-(2,6-dichlorophenoxy)-propionic acid-N-(2-aminoethyl)-amide. A solution of 63.0 g ($\triangleq$0.5155 mols) of 4-dimethylaminopyridine is then added dropwise very slowly at 0° C. with stirring and the mixture is further stirred for 36 hours at room temperature after the solution has been added. After working up and after purification by column chromatography (silica gel-dry column, eluant: chloroform/tetrahydrofuran 3:1), 16.0 g of (+)-2-[1-(2,6-dichlorophenoxy)ethyl]-1,3-diazacyclopent-2-ene $C_{11}H_{12}Cl_2N_2O$ [259.1], are obtained, Mp: 127°–128° C.: $[\alpha]_D^{20} = +80.6°$ (c=1/ethanol).

(+)-2-[1-(2,6-dichlorophenoxy)-ethyl]-1,3-diazacyclopent-2-ene hydrochloride 10.0 g of (+)-2-[1-(2,6-dichlorophenoxy)-ethyl]-1,3-diazacyclopent-2-ene are dissolved in 40 ml of propan-2-ol and are mixed with 40 ml of a saturated solution of hydrogen chloride in propan-2-ol. After a corresponding working-up operation, 7.8 g of (+)-2-[1-(2,6-dichlorophenoxy)-ethyl]-1,3-diazacyclopent-2-ene hydrochloride $C_{11}H_{12}Cl_2N_2O \cdot HCl$ [295.6] are obtained, Mp.: 229° C. $[\alpha]_D^{20} = +33.4°$ (c=1/ethanol).

EXAMPLE 2

Synthesis of
(+)-2-[1-(2,6-dichlorophenoxy)-ethyl]-1,3-diazacyclopentene-(2)-hydrochloride The starting material is described in Example 1, stage 2.

(−)-2-)2,6-dichlorophenoxy)-propionic acid amide

Ammonia is introduced at room temperature and with stirring for 24 hours into a solution of 55 g ($\triangleq$0.2091 mols) of (+)-2-(2,6-dichlorophenoxy)-propionic acid ethylester in 100 ml of ethanol saturated with ammonia. After working up, 35.0 of (−)-2-(2,6-dichlorophenoxy)-propionic acid amide $C_9H_9Cl_2NO_2$ [234.1] are obtained, Mp.: 192° C. $[\alpha]_D^{20} = -20.3°$ (c=1/acetone)

(+)-2-(2,6-dichlorphenoxy)-propionitrile

A solution of 17.9 g ($\triangleq$0944 mols) of titanium tetrachloride in 50 ml of absolute chloroform and 7 ml of tetrahydrofuran is mixed with 11.0 g ($\triangleq$0.0470 mols) of (−)-2-(2,6-dichlorophenoxy)-propionic acid amide. A solution of 19.0 g ($\triangleq$0.1877 mols) of 4-methylmorpholine is then added dropwise very slowly with stirring at 0° C. and after the solution has been added, the contents of the flask are further stirred for 24 hours at 30° C. After working up, 7.5 g of (+)-2-(2,6-dichlorophenoxy)-propionitrile $C_9H_7Cl_2NO$ [216.1] are obtained, $Bp_{0.1}$: 81° C. $[\alpha]_D^{20} = +76°$ (undiluted).

(+)-2-[1-(2,6-dichlorophenoxy)-ethyl]-1,3-diazacyclopent-2-ene 22.0 g (=0.1018 mols) of (+)-2-(2,6-dichlorophenoxy)-propionitrile are converted into (+)-2-(2,6-dichlorophenoxy)-propionimido acid ethylester-hydrochloride at 0° C. with 4.7 g ($\triangleq$0.1018 mols) of ethanol in 50 ml of absolute chloroform by intoducing hydrogen chloride. This product is then dissolved in 20 ml of ethanol after removing the solvent under vacuum at 20° C. and is cyclised with 6.6 g ($\triangleq$0.11 mol) of 1,2-diaminoethane into (+)-2-[1-(2,6-dichlorophenoxy)ethyl]-1,3-diazacyclopent-2-ene $C_{11}H_{12}Cl_2N_2O$ [259.1]. After working up, 17 g of product are obtained.

Mp. 128° C. $[\alpha]_D^{20} = +80.4°$ (c=1/ethanol)

(+)-2-[1-(2,6-dichlorophenoxy)-ethyl]-1,3-diazacyclopentene-(2)-hydrochloride 4.0 g of (+)-2-[1-(2,6-dichlorophenoxy)-ethyl]-1,3-diazacyclopent-2-ene are dissolved in 16 ml of propan-2-ol and are mixed with 16 ml of a saturated solution of hydrogen chloride in propan-2-ol. 3.3 g of (+)-2-[1-(2,6-dichlorophenoxy)-ethyl]-1,3-diazacyclopent-2-ene hydrochloride $C_{11}H_{12}Cl_2N_2O \cdot HCl$ [295.6] are obtained, Mp. 229° C. $[\alpha]_D^{20} = +33.2°$ (c=1/ethanol)

EXAMPLE 3

Production of (+)-2-[1-(2,6-dichlorophenoxy)-ethyl]-1,3-diazacyclopent-2-ene by resolution of (±)-2-[1-(2,6-dichlorophenoxy)-ethyl]1,3-diazacyclopent-2-ene with (+)-dibenzoyl tartaric acid 10 g of (±)-2-[1-(2,6-dichlorophenoxy)-ethyl]-1,3-diazacyclopent-2-ene are dissolved in 400 ml of acetone at room temperature, are added with stirring to a solution of 14.5 g of (+)-dibenzoyl tartaric acid $[\alpha]_D^{20} = +110°$ (c=1/ethanol 96%) in 2000 ml of acetone and are left to stand for 24 hours at 21° C. without stirring. The resulting salt (12.8 g) is present as (+)-dibenzoyl tartrate of the concentrated (+) base $[[\alpha]_D^{20} = +65.6°$ c=1/ethanol)]. After neutralisation with saturated sodium carbonate solution and after extraction with dichloromethane, 6.9 g of base are obtained from this salt and after being dissolved in 550 ml of acetone, are again mixed with a solution of 10.0 g of (+)-dibenzoyl tartaric acid in 2200 ml of acetone. After 24 hours, 9.8 g of (+)-dibenzoyl tartrate of the (+) base $[[\alpha]_D^{20} = +67.5°$ (c=1/ethanol)] which is now already highly concentrated, are obtained. Further purification is carried out by recrystallising 9.7 g of this salt from 250 ml of hot ethanol at 60° C. After 24 hours (21° C.), 4.6 g of (+)-dibenzoyl tartrate of the (+) base $[[\alpha]_D^{20} = +72.6°$ (c=1/ethanol)] are obtained. The second recrystallisation of 4.5 g of this salt from 70 ml of hot ethanol at 60° C. produces after 24 hours (21° C.) 2.9 g of (+)-2-[1-(2,6-dichlorophenoxy)-ethyl]-1,3-diazacyclopent-2-ene (+)-dibenzoyl tartrate, $[[\alpha]_D^{20} = +77.8°$ (c=1/ethanol)]. 1.3 g of pure (+) base are released from 2.8 g of this salt using 15 ml of saturated sodium carbonate solution and 40 ml of dichloromethane and are dissolved in 2.5 ml of propan-2-ol, mixed with 2.5 ml of a saturated solution of hydrogen chloride in propan-2-ol and are converted into the hydrochloride. The following is obtained: 0.9 g of (+)-2-[1-(2,6-dichlorophenoxy)-ethyl]-1,3-diazacyclopentene(2)-hydrochloride $C_{11}H_{12}Cl_2N_2O \cdot HCl$ [295.6], Mp. 228°–229° C. $[\alpha]_D^{20} = +33.4°$ (c=1/ethanol).

What we claim is:

1. Method for the treatment of human beings suffering from migraine, comprising administering to such human beings between 0.05 to 50 mg of (+)-2-[1-(2.6-dichlorophenoxy)-ethyl]-1.3-diazacyclopent-2-ene per each dose unit or the equivalent amount of a pharmaceutically acceptable acid addition salt thereof.

2. Method for the treatment of human beings suffering from migraine, comprising administering to such human beings between 0.05 to 50 mg of (+)-2-[1-(2.6-dichlorophenoxy)-ethyl]-1.3-diazacyclopent-2-ene hydrochloride per each dose unit.

3. A composition for treatment of human beings suffering from migraine comprising (+)-2-[1-(2.6-dichlorophenoxy)-ethyl]-1.3-diazacyclopent-2-ene as the active substance in an amount of 0.05 to 50 mg per dose unit and a pharmaceutically acceptable carrier.

4. A composition for treatment of human beings suffering from migraine comprising (+)-2-[1-(2.6-dichlorophenoxy)-ethoxy]-1.3-diazacyclopent-2-ene hydrochloride as the active substance in an amount of 0.05 to 50 mg per dose unit and a pharmaceutically acceptable carrier.

* * * * *